United States Patent
Wilson-Wirth et al.

(10) Patent No.: US 10,485,535 B2
(45) Date of Patent: Nov. 26, 2019

(54) HIGH-STRENGTH BIOABSORBABLE SUTURE

(71) Applicant: Tornier, Inc., Bloomington, MN (US)

(72) Inventors: Corey R. Wilson-Wirth, Bloomington, MN (US); Dale R. Peterson, Bloomington, MN (US); Kevin L. Ohashi, Bloomington, MN (US)

(73) Assignee: Tornier, Inc., Bloomington, MN (US)

( * ) Notice: Subject to any disclaimer, the term of this patent is extended or adjusted under 35 U.S.C. 154(b) by 127 days.

(21) Appl. No.: 15/039,167

(22) PCT Filed: Nov. 26, 2014

(86) PCT No.: PCT/US2014/067760
§ 371 (c)(1),
(2) Date: May 25, 2016

(87) PCT Pub. No.: WO2015/094619
PCT Pub. Date: Jun. 25, 2015

(65) Prior Publication Data
US 2017/0156727 A1    Jun. 8, 2017

Related U.S. Application Data

(60) Provisional application No. 61/918,083, filed on Dec. 19, 2013.

(51) Int. Cl.
*A61B 17/06* (2006.01)
*A61B 17/04* (2006.01)
(Continued)

(52) U.S. Cl.
CPC .... *A61B 17/06166* (2013.01); *A61B 17/0401* (2013.01); *A61B 90/92* (2016.02);
(Continued)

(58) Field of Classification Search
CPC .............. A61B 17/04; A61B 17/06166; A61B 2017/00663; A61F 2/08; A61L 17/00
(Continued)

(56) References Cited

U.S. PATENT DOCUMENTS 6,759,219 B2    7/2004 Hein et al.
6,838,492 B2    1/2005 Williams et al.
(Continued)

FOREIGN PATENT DOCUMENTS

EP    1 042 388    11/2006
EP    0 981 381    2/2007
(Continued)

OTHER PUBLICATIONS

European Search Report issued in European Patent Application No. 14872791.0, dated Jul. 14, 2017, in 4 pages.
(Continued)

*Primary Examiner* — Melanie R Tyson
(74) *Attorney, Agent, or Firm* — Knobbe, Martens, Olson & Bear, LLP

(57) ABSTRACT

A suture is provided having a multifilament sheath disposed thereabout a monofilament core. The multifilament sheath includes a plurality of yarns, and each of the plurality of yarns includes a plurality of threads. Further, the suture includes poly-4-hydroxybutyrate (P4HB).

20 Claims, 8 Drawing Sheets

(51) Int. Cl.
*A61L 17/10* (2006.01)
*A61B 90/92* (2016.01)
*A61F 2/08* (2006.01)
*A61B 17/00* (2006.01)

(52) U.S. Cl.
CPC ... *A61L 17/105* (2013.01); *A61B 2017/00004* (2013.01); *A61B 2017/00526* (2013.01); *A61B 2017/00893* (2013.01); *A61B 2017/044* (2013.01); *A61B 2017/0409* (2013.01); *A61B 2017/0414* (2013.01); *A61F 2/08* (2013.01); *A61F 2210/0004* (2013.01); *A61F 2250/0067* (2013.01)

(58) Field of Classification Search
USPC .................................................. 606/228–231
See application file for complete search history.

(56) References Cited

U.S. PATENT DOCUMENTS

| | | |
|---|---|---|
| 6,867,247 B2 | 3/2005 | Williams et al. |
| 6,867,248 B1 | 3/2005 | Martin et al. |
| 7,229,804 B2 | 6/2007 | Huisman et al. |
| 7,244,442 B2 | 7/2007 | Williams et al. |
| 7,268,205 B2 | 9/2007 | Williams et al. |
| 7,906,135 B2 | 3/2011 | Williams et al. |
| 8,084,125 B2 | 12/2011 | Rizk |
| 8,231,889 B2 | 7/2012 | Williams et al. |
| 2011/0318395 A1 | 12/2011 | Martin et al. |
| 2012/0053689 A1* | 3/2012 | Martin ................ A61L 17/105 623/8 |
| 2012/0059468 A1* | 3/2012 | Mattern ............... A61F 2/0811 623/13.14 |
| 2013/0231700 A1* | 9/2013 | Gedet ................. A61L 17/145 606/228 |

FOREIGN PATENT DOCUMENTS

| | | |
|---|---|---|
| EP | 1 163 019 | 10/2007 |
| EP | 2 196 484 | 6/2010 |
| EP | 2 221 069 | 8/2010 |
| WO | WO 2015/094619 | 6/2015 |

OTHER PUBLICATIONS

Barber et al., "Sutures and Suture Anchors—Update 2006", *Arthroscopy: The Journal of Arthroscopic and Related Surgery*, Oct. 2006, vol. 22, No. 10, pp. 1063-1069.

Bruker et al., In-Vivo Performance—Orthocord™ Breaking Strength Retention and Histomorphologic Observations, *DePuy Mitek, Inc.*, 2004, in 2 pages.

International Search Report and Written Opinion issued in PCT Application No. PCT/US2014/067760, dated Mar. 3, 2015, in 13 pages.

Martin et al. "Medical applications of poly-4-hydroxybutyrate: a strong flexible absorbable 1-20 biomaterial", *Biochemical Engineering Journal*, 2003, vol. 16, pp. 97-105.

Wüst et al., "Mechanical and Handling Properties of Braided Polyblend Polyethylene Sutures in Comparison to Braided Polyester and Monofilament Polydioxanone Sutures", *Arthroscopy: The Journal of Arthroscopic and Related Surgery*, Nov. 2006, vol. 22, No. 11, pp. 1146-1153.

* cited by examiner

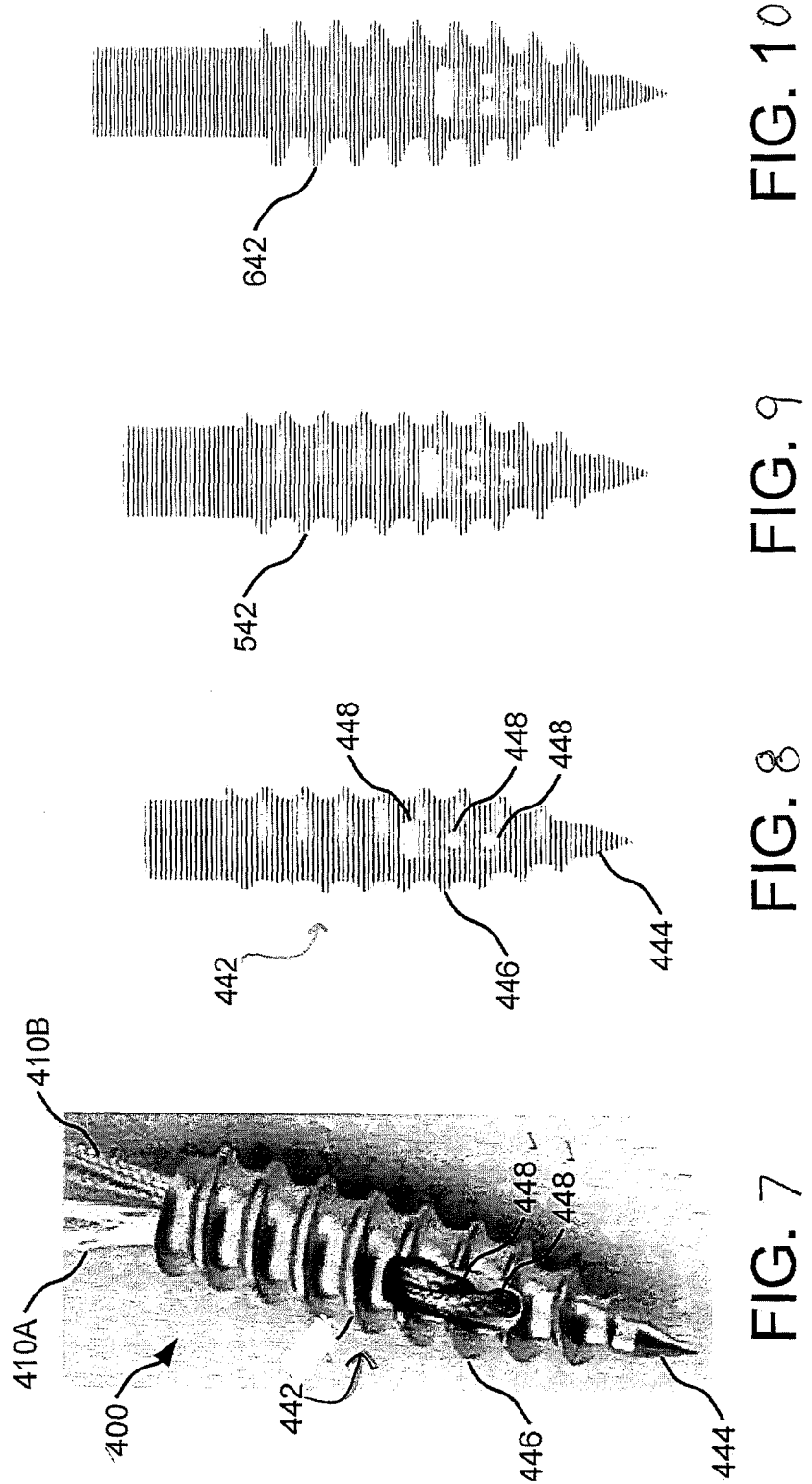

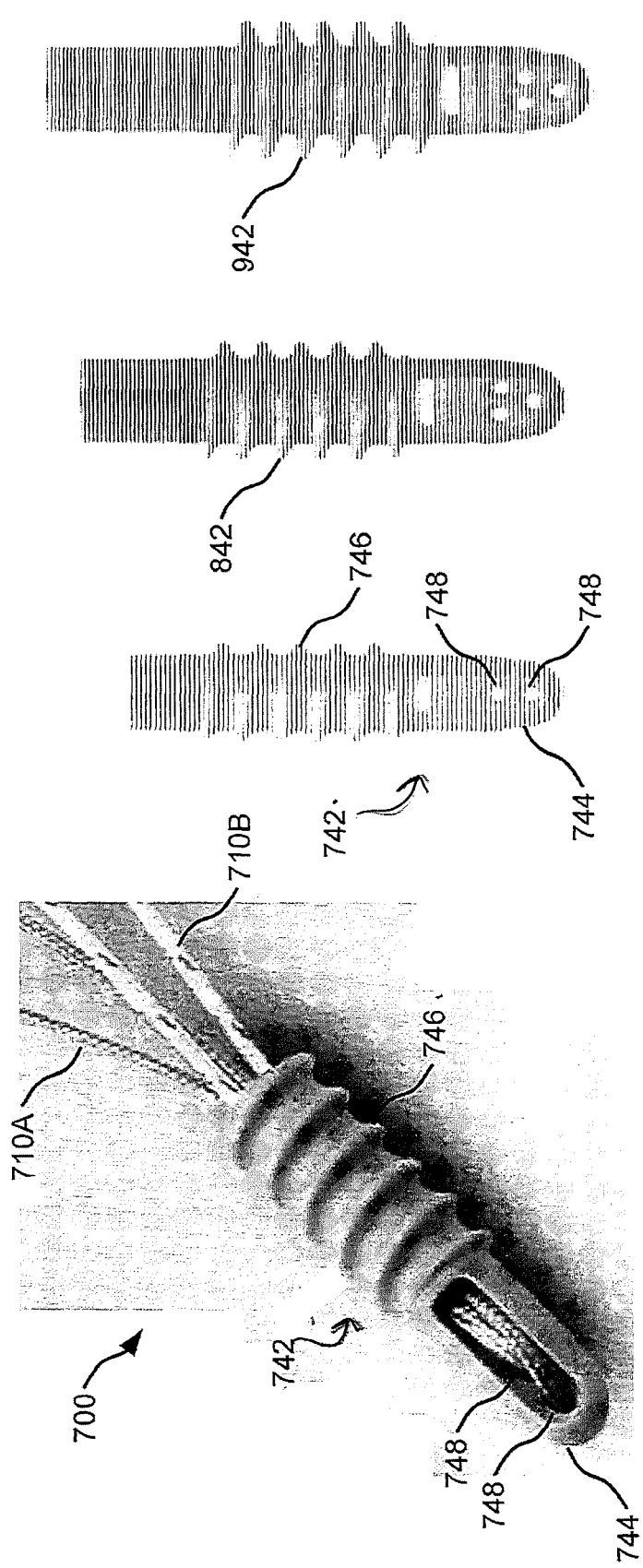

HIGH-STRENGTH BIOABSORBABLE SUTURE

INCORPORATION BY REFERENCE TO ANY PRIORITY APPLICATIONS

The present application is a national phase of PCT Application No. PCT/US2014/067760, filed Nov. 26, 2014 titled "HIGH-STRENGTH BIOABSORBABLE SUTURE," which claims priority benefit under 35 U.S.C. § 119(e) to U.S. Provisional Patent Application Ser. No. 61/918,083, filed Dec. 19, 2013, both of which are incorporated by reference in their entirety herein. Any and all applications for which a foreign or domestic priority claim is identified in the Application Data Sheet as filed with the present application are hereby incorporated by reference under 37 CFR 1.57.

TECHNICAL FIELD

The present invention relates to sutures used in medical procedures. In particular, the present invention relates to high-strength bioabsorbable sutures used in orthopedic procedures.

BACKGROUND

"High strength" sutures are typically used in orthopedic procedures due to the relatively high loading requirements in such applications. Currently, high strength sutures are formed using non-absorbable materials, such as ultra-high molecular weight polyethylene (UHMWPE) and the like, or a combination of non-absorbable yarns and bioabsorbable yarns which may be woven or braided together. As such, high strength sutures are typically considered either permanent sutures (if formed by non-absorbable materials) or partially permanent (formed from a combination of non-absorbable and absorbable materials). Improvements in the field are desired.

SUMMARY

A suture is provided including a multifilament sheath having a plurality of yarns, the plurality of yarns comprising poly-4-hydroxybutyrate; and a monofilament core comprising poly-4-hydroxybutyrate, wherein the multifilament sheath is disposed thereabout the monofilament core.

Sutures may have an ultimate tensile strength of from about 140 Newtons to about 190 Newtons, and an elongation to break of about 30 percent to about 50 percent.

Sutures may also be provided having a bioabsorbable monofilament core and a bioabsorbable multifilament sheath disposed thereabout the bioabsorbable monofilament core wherein the suture consists essentially of poly-4-hydroxybutyrate.

Methods for manufacturing sutures in accordance with the present invention are also disclosed.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 7 illustrates a partial perspective view of a suture/anchor apparatus according to an embodiment of the present invention;

FIG. 8 illustrates a side view of the anchor of the suture/anchor apparatus of FIG. 7;

FIG. 9 illustrates a side view of another anchor of a suture/anchor apparatus according to an embodiment of the present invention;

FIG. 10 illustrates a side view of another anchor of a suture/anchor apparatus according to an embodiment of the present invention;

FIG. 11 illustrates a partial perspective view of a suture/anchor apparatus according to an alternate embodiment of the present invention;

FIG. 12 illustrates a side view of the anchor of the suture/anchor apparatus of FIG. 11;

FIG. 13 illustrates a side view of another anchor of a suture/anchor apparatus according to an embodiment of the present invention;

FIG. 14 illustrates a side view of an alternate anchor of a suture/anchor apparatus according to an embodiment of the present invention;

Figure 1:
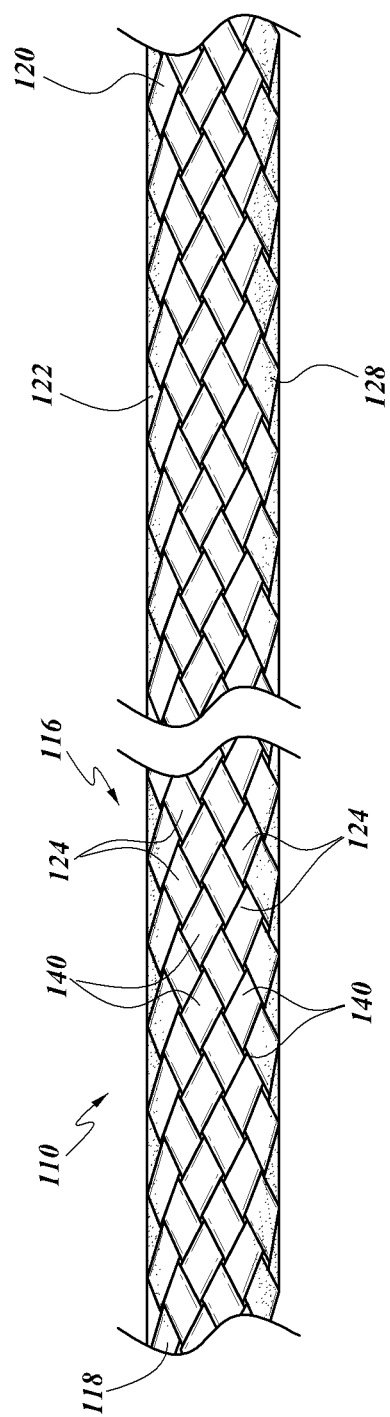
FIG. 1 illustrates a partial side view of a suture according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
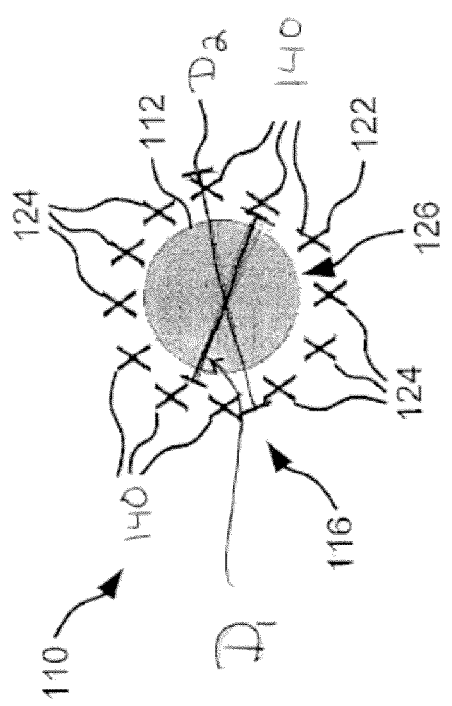
FIG. 2 illustrates a schematic cross-sectional view of the suture of FIG. 1.

FIGS. 1 and 2 illustrate a suture 110 according to an embodiment of the present invention. The suture 110 generally includes a body 116 which extends between a first end 118 and a second end 120 of the suture 110. In particular, the body 116 comprises a core 112 surrounded by a multifilament sheath 122. The multifilament sheath 122 further includes a plurality of individual threads (not labeled) which may be woven, braided or otherwise entangled to form yarns 124, 140. In some embodiments, the suture 110 may include a needle (not illustrated) disposed on at least one of the first end 118 or the second end 120 of the suture.

Referring back to FIGS. 1 and 2, the suture 110 includes a multifilament sheath 122 surrounding the core 112. In particular, the multifilament sheath 122 includes from about eight yarns to about twelve yarns. In particular, a multifilament sheath 122 including 7, 8, 9, 10, 11, 12 and 13 yarns are contemplated. In embodiments, the sheath 122 may include about twelve yarns. In other embodiments, the sheath 122 includes about eight yarns. In particular, the yarns 125, 140 having a denier of 100, 110, 120, 130, and 140 and any denier in between these ranges are contemplated. Further, thread counts of 30, 35, 40, 45, 50, 55, 60, 65, 70, 75, and 80 are contemplated. In one particular embodiment, each yarn 124, 140 is about 120 denier and includes about 60 threads.

Numerous braid patterns can be used in forming the multifilament sheath including "one yarn under two yarns over," "one yarn over two yarns under," "two yarns over two yarns under," "one yarn under one yarn over." Specifically, the yarns 124, 140 may be braided with one another in a specified pattern, such as, for example, in a repeating "over two, under two" pattern, to form the multifilament sheath 122. Other patterns are also envisioned and within the purview of those skilled in the art. Alternatively, the yarns 124, 140 may be comingled, knitted, woven, or otherwise entwined to form the multifilament sheath.

Further, sutures of the present disclosure may have from about 54 to about 71 picks per inch. In particular, sutures may have 54.3, 55.8, 56, 64.5, 64.7, 69.7, and 70.5 picks per inch. Further, depending on multifilament sheath construct, the picks per inch may vary. In specific embodiments, sutures of the present disclosure may have about 70.5 picks per inch.

In some embodiments, some of the yarns 124, 140 or threads may be provided with different colors to provide a visible pattern on the suture 110. For example, two of the yarns 124, 140 may have violet colored threads and ten of the yarns 124, 140 may have natural colored threads.

The sheath 122 defines an inner or internal passageway 126 (see FIG. 2) of the sheath 122 that houses the core 112. The inner passageway 126 has a diameter $D_1$ that is sized to receive the core 112. Stated otherwise, D is the inner diameter of the multifilament sheath 122. In embodiments, $D_1$ is equal to or greater than the diameter of the monofilament core. In some embodiments, at least one of the yarns 124, 140 contact the core 112. The outermost portion of the sheath 122 also defines an outer diameter $D_2$ of the suture 110.

The core 112 and sheath 122 are provided with a bioabsorbable polymeric material that facilitates high suture strength. Sutures described herein are formed from poly-4-hydroxybutyrate (P4HB). Poly-4-hydroxybutyrate is a polyester having the chemical structure illustrated below.

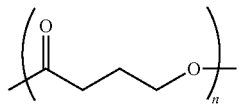

In particular, the monofilament core 112 is comprised of P4HB. Additionally, threads and yarns of the multifilament sheath 122 are comprised of P4HB. Stated otherwise, sutures 110 of the present disclosure include a monofilament core 112 formed of P4HB and each thread, and in turn, all of the yarns are formed entirely of P4HB.

In alternate embodiments, sutures of the present disclosure may be provided without a core. In other words, the sutures may be provided with a multifilament sheath as described herein, having an inner passageway which is hollow and absent of a monofilament core. It should be noted that when the core is removed, the multifilament sheath maintains a cylindrical configuration in some embodiments, rather than a flat or otherwise collapsed configuration. Sutures of smaller sizes, for example, sizes 2-0 and 0 (see USP guidelines) may be provided as a multifilament sheath, absent of a monofilament core.

Methods for manufacturing P4HB are within the purview of those skilled in the art and can be found, for example in 'Medical applications of poly-4-hydroxybutyrate: a strong absorbable biomaterial' (Biochemical Engineering Journal 16 (2003) 97-105), the contents of which are incorporated by reference herein. In particular, the core 112 and the threads may be obtained, for example, from Tepha Inc. of Cambridge, Mass., USA.

Suture 110 may be formed using any technique within the purview of those skilled in the art, such as, for example, extrusion, molding and/or gel spinning. Threads of the sheath may be drawn, oriented, crinkled, twisted, commingled or air entangled to form yarns as part of the suture forming process. In one embodiment, the suture is produced by braiding the multifilament sheath around the monofilament core. The braiding may be done by any method within the purview of those skilled in the art. Alternatively, the multifilament sheath may be formed and subsequently the monofilament core inserted therein.

Once the suture is constructed, it can be sterilized by any means within the purview of those skilled in the art.

In some embodiments, the suture 110 may include therapeutic agents in the form of, by example, a coating. Therapeutic agents include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (beta.-IFN, .alpha.-IFN and .gamma.-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In some embodiments, the therapeutic agent includes at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentine, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillamine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbital sodium, clorazepate dipotassium, and trimethadione); antiparkinson agents (e.g., ethosuximide); antihistaminesiantipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime axetil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocrormil sodium; metaproterenol sulfate; albuterol; flunisolide; fluticasone proprionate; steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or antisense nucleic adds encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, omeprazole, fluoxetine, lisinopril, tramadol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the drug may be water soluble. In other embodiments, the drug may not be water soluble. Alternatively, the suture 110 may be coated with other absorbable or non-bioabsorbable materials, such as polymers, which may after suture degradation. Polymers for coatings may be comprised of polycaprolactone, poly lactic acid, poly glycolic acid, polyethylene oxide, polydioxanone, or other biodegradable materials. Alternatively, non-absorbable polymers may be applied as coatings for sutures described herein. Coatings may be used to alter other mechanical properties of the sutures such as handling characteristics (e.g., knot run down, knot security). Suitable non-absorbable and bioabsorbable polymer coatings are within the purview of those skilled in the art.

Referring back to FIGS. 1 and 2, and as previously mentioned, the suture 110 includes a core 112 and a multifilament sheath 122. The core 112 may be from about a size 0 to about a size 5-0, per USP (United States Pharmacopia) guidelines. In some embodiments, the core 112 is about a size 0 while in other embodiments, the core 112 is about a size 5-0. Core sizes of 2-0, 3-0, 4-0, and also any fractional size between sizes 0 and 5-0 are also contemplated. Additionally, the outer diameter $D_2$ may be sized to provide the suture 110 with an overall USP size of from about size 2 to about size 2-0. Overall sized of size 1, 0, 1-0, and also any fractional size between sizes 2 and 2-0 are also contemplated. In some embodiments, the outer diameter $D_2$ may be sized to provide the suture 110 with an overall size of about size 2. In other embodiments, the outer diameter $D_2$ may be sized to provide the suture 110 with an overall size of about size 2-0. In some embodiments, the outer diameter $D_2$ may be sized to provide the suture 110 with an overall USP size of from about size 2 to about size 2-0. In some embodiments, the outer diameter $D_2$ may be sized to provide the suture 110 with an overall size of about size 2. In other embodiments, the outer diameter $D_2$ may be sized 10 provide the suture 110 with an overall size of about size 2-0.

Sutures 110 of the present disclosure have an ultimate tensile strength of from about 140 Newtons to about 190 Newtons. In particular, sutures 110 having an ultimate tensile strength of at least 130, 135, 140, 145, 150, 155, 160, 165, 170, 175, 180, 185, 190, 195, and 200 Newtons are contemplated. In specific embodiments, the suture has an ultimate tensile strength of about 180 Newtons. It should be noted that the ultimate tensile strength values described herein are for straight pull testing of the sutures, unless otherwise indicated. Straight pull testing as referenced herein means that the suture had been tested, in this case, tension tested, in a unknotted, straight configuration.

Further, sutures 110 are provided with an elongation to break of about 30 percent to about 50 percent. In particular, sutures 110 having an elongation to break of at least 25, 30, 35, 40, 45, 50, 55, 60, 65, and 70 percent are contemplated. In specific embodiments, the suture has an elongation to break of at least about 34 percent. It should be noted that the elongation to break values described herein are for straight tension testing of the sutures, unless otherwise indicated.

In some embodiments, the suture 110 may have a strength resorption (relative to the ultimate tensile strength) of about 64.9 percent at two weeks after implantation, about 67.1 percent at four weeks after implantation, about 67.0 percent at eight weeks after implantation, about 44.9 percent at 12 weeks after implantation, about 18.8 percent at 26 weeks after implantation, and about 0.6 percent at 52 weeks after implantation. For example, strength resorption at 2 weeks is defined as the strength of the suture after 2 weeks implantation in vivo as a percentage of the strength of the suture at the start of or prior to implantation in vivo.

It should be noted that for different surgical procedures, alternate strength and resorption profiles may be preferred. Accordingly it is envisioned that for certain procedures the sutures comprising P4HB may be modified with other materials, such as, for example, coatings.

The suture 110 may be coupled to tissue of a patient, or subject, in medical procedures including orthopedic procedures, such as repairing rotator cuff tears. It should be noted that various size sutures are envisioned for other surgical procedures. The sutures described herein may be configured or arranged for use in various orthopedic applications or used together with other components commonly used in different applications. For example, the sutures described herein may be configured for use as scaffolds, meshes, wound closure devices, and the like. As another example, the sutures described herein may be used together with a suture passer, such as, for example, the ArthroTunneler™ device available from Tornier, Inc. (Bloomington, Minn.).

Figure 3:
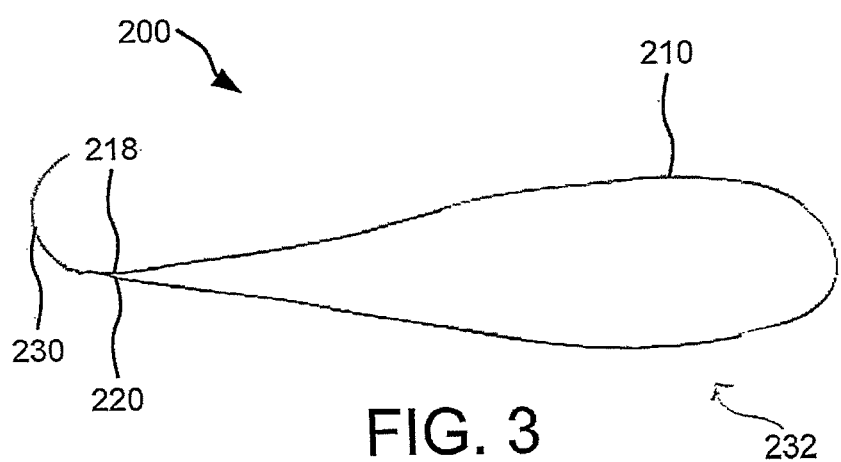
FIG. 3 illustrates a side view of a suture apparatus according to an embodiment of the present invention.

FIG. 3 illustrates a suture apparatus 200 according to an embodiment of the present invention. The suture apparatus 200 includes a suture 210 that may be, for example, any of the sutures described herein. The first end 218 and/or the second end 220 of the suture 210 connect to a needle 230. As such, the suture 210 forms a loop 232 connected to the needle 230. In some embodiments, the needle 230 has an arcuate shape. In one example, the needle 230 may be a half-circle taper point needle. Other needles and needle shapes are also contemplated such as, for example, straight and sickle.

Figure 4:
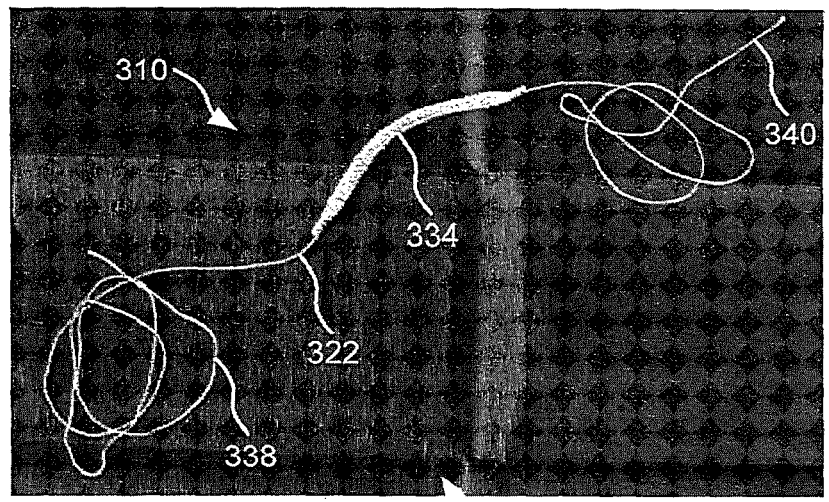
FIG. 4 illustrates a side view of a suture according to an embodiment of the present invention.
Figure 5:
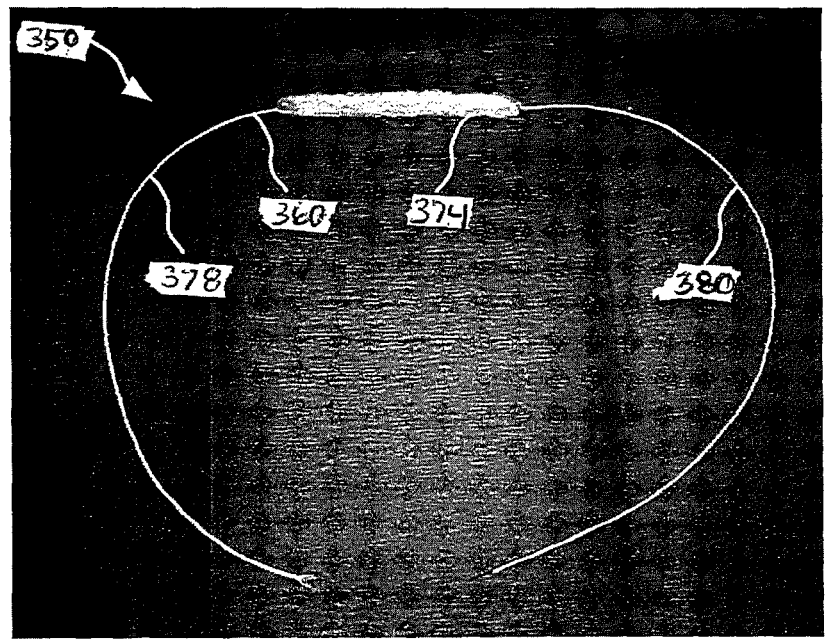
FIG. 5 illustrates a partial side view of another embodiment of a suture according to the present invention.
Figure 6:
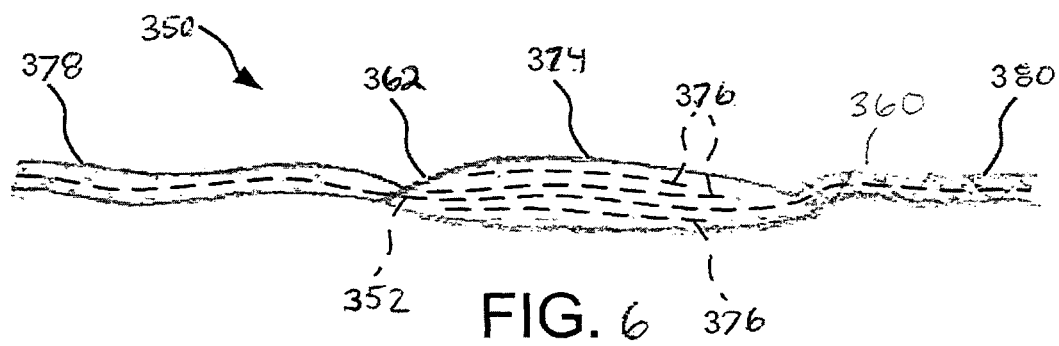
FIG. 6 illustrates a partial side view of the suture of FIG. 5.

FIG. 4 illustrates a suture 310 according to an embodiment of the present invention. The suture 310 includes monofilament core that is surrounded by a multifilament sheath. However, the suture 310 also includes an enlarged portion 334 that is thicker or larger in diameter than other portions, such as portion 322 of the suture 310. The enlarged portion 334 includes the sheath and the core. In the embodiment illustrated, the enlarged portion 334 is larger in diameter than either end portion 340, 338. In specific embodiments, the enlarged portion 334 is disposed on an inner portion of the suture (rather than at one of the ends 340, 338), as illustrated in FIGS. 4-6. FIG. 4 is also disclosed in US 2012/0059468 (FIG. 1), assigned to Tornier, Inc (Bloomington, Minn.) the contents and description of FIG. 1 are incorporated by reference herein.

FIGS. 5-6 illustrate a similar embodiment to FIG. 4. The suture 350 includes a monofilament core 352 surrounded by a multifilament sheath 362. The suture 350 also includes an enlarged portion 374 that has a larger diameter than other portions such as, for example, portion 360, of the suture 350. The enlarged portion includes both the sheath 362 and the core 352. Further, the sheath 362 surrounds one or more additional filaments 376 (see FIG. 6) at the enlarged portion 374. The additional filaments 376 may be, for example, monofilaments or multifilament yarns. The additional filaments 376 may include one or more of various materials, for example, a polymer, such as P4HB. In one particular embodiment, the all of the filaments 376 comprise P4HB. In certain embodiments, the enlarged portion 374 is disposed between opposite ends 378 and 380 of the suture 350.

FIGS. 7 and 8 illustrate a suture/anchor apparatus 400 according to an embodiment of the present invention. The apparatus 400 includes one or more sutures that may be, for example, any of the sutures described herein in combination with a suture anchor 442. In some embodiments and as shown in FIG. 7, the apparatus 400 may include two sutures 410A and 410B, although other numbers of sutures may be used. The apparatus 400 also includes the suture anchor 442 coupled to the sutures 410A and 410B. The anchor 442 may be, for example, an Insite® FT Titanium anchor, disclosed in US 2012/0053626 assigned to Tornier, Inc (Bloomington, Minn.), the contents of which are incorporated by reference herein. In some embodiments, the anchor 442 is titanium. The anchor 442 includes a self-drilling starter tip 444 and screw threads 446 for engaging bone of a subject. In some embodiments, the anchor 442 includes an inner chamber (not shown) and one or more eyelets 448 for coupling to the sutures 410A and 410B. Suture anchors as described herein are primarily for orthopedic procedures, although other procedures are envisioned and within the scope of this application.

FIGS. 9 and 10 illustrate other anchors 542 and 642, respectively, of suture/anchor apparatus for use with sutures of the present invention. The anchors 542 and 642 are generally similar to the anchor 442, although each of the anchors 442, 542, and 642, has different dimensions (for example, diameters of 4.5 mm, 5.5 mm, and 6.5 mm, respectively) and/or numbers of features (for example, a different number of eyelets for coupling to sutures).

FIGS. 11 and 12 illustrate a suture/anchor apparatus 700 according to another embodiment of the present invention. The apparatus 700 includes one or more sutures that may be, for example, any of the sutures described herein. In some embodiments and as shown in FIG. 11, the apparatus 700 may include two sutures 710A and 710B, although other numbers of sutures may alternatively be used. The apparatus 700 also includes an anchor 742 coupled to the sutures 710A and 710B. The anchor 742 may be, for example, an Insite® FT PEEK-OPTIMA® anchor, disclosed in US 2012/0053626, assigned to Tornier, Inc (Bloomington, Minn.), the contents of which are incorporated by reference herein. In some embodiments, the anchor 742 includes PEEK-OPTIMA® material available from Invibio Limited. In some embodiments, the anchor 742 includes a "bullet-shaped" tip 744 to facilitate ease of insertion into a pre-formed bone hole. In some embodiments, the anchor 742 includes screw threads 746 for engaging bone of a subject. In some embodiments, the anchor 742 includes an inner chamber (not shown) and one or more eyelets 748 for coupling to the sutures 710A and 710B.

FIGS. 13 and 14 illustrate other anchors 842 and 942, respectively, of suture/anchor apparatus for use with sutures the present invention. The anchors 842 and 942 are generally similar to the anchor 742, although each of the anchors 742, 842, and 942, has different dimensions (for example, diameters of 4.5 mm, 5.5 mm, and 6.5 mm, respectively) and/or numbers of features (for example, a different number of eyelets for coupling to sutures).

The sutures described herein may be used in conjunction with various other types of anchors or "stops". For example, the sutures described herein may be used in conjunction with the Endobutton™ available from Smith & Nephew, Inc. (Andover, Mass.), the EZLoc™ femoral fixation device available from Biomet, Inc. (Warsaw, Ind.), the Toggle-Loc™ femoral fixation device available from Biomet, Inc. (Warsaw, Ind.), and the like.

Figure 15:
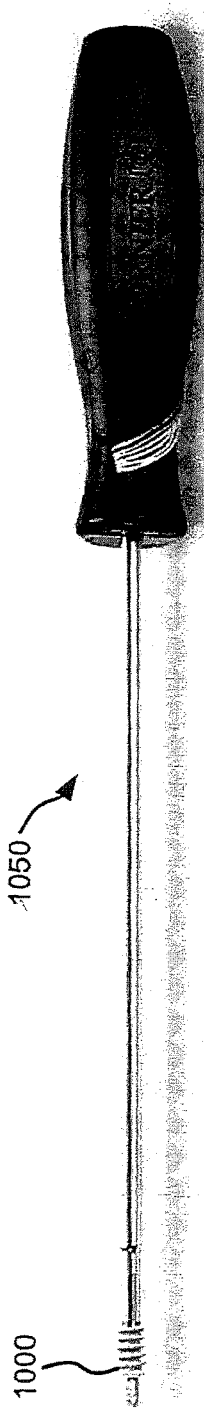
FIG. 15 illustrates a side view of a suture/anchor apparatus insertion tool for use with the present invention.

FIG. 15 illustrates an insertion tool 1050 that detachably supports a suture/anchor apparatus 1000. The suture/anchor apparatus 1000 may be, for example, any of the suture/anchor apparatus described herein. In particular, the insertion tool 1050 may be used to interface with and install a suture anchor in the bone of a patient. More specifically, the distal end of the insertion tool 1050 can be inserted into a proximal end of the suture anchor in order to transmit thereto a rotary movement and torque. A more detailed description of the insertion tool 1050 may be found in US 20012/0053626 (FIG. 18 and description thereof), assigned to Tornier. In (Bloomington, Minn.), the contents of which are incorporated by reference herein.

Figure 16:
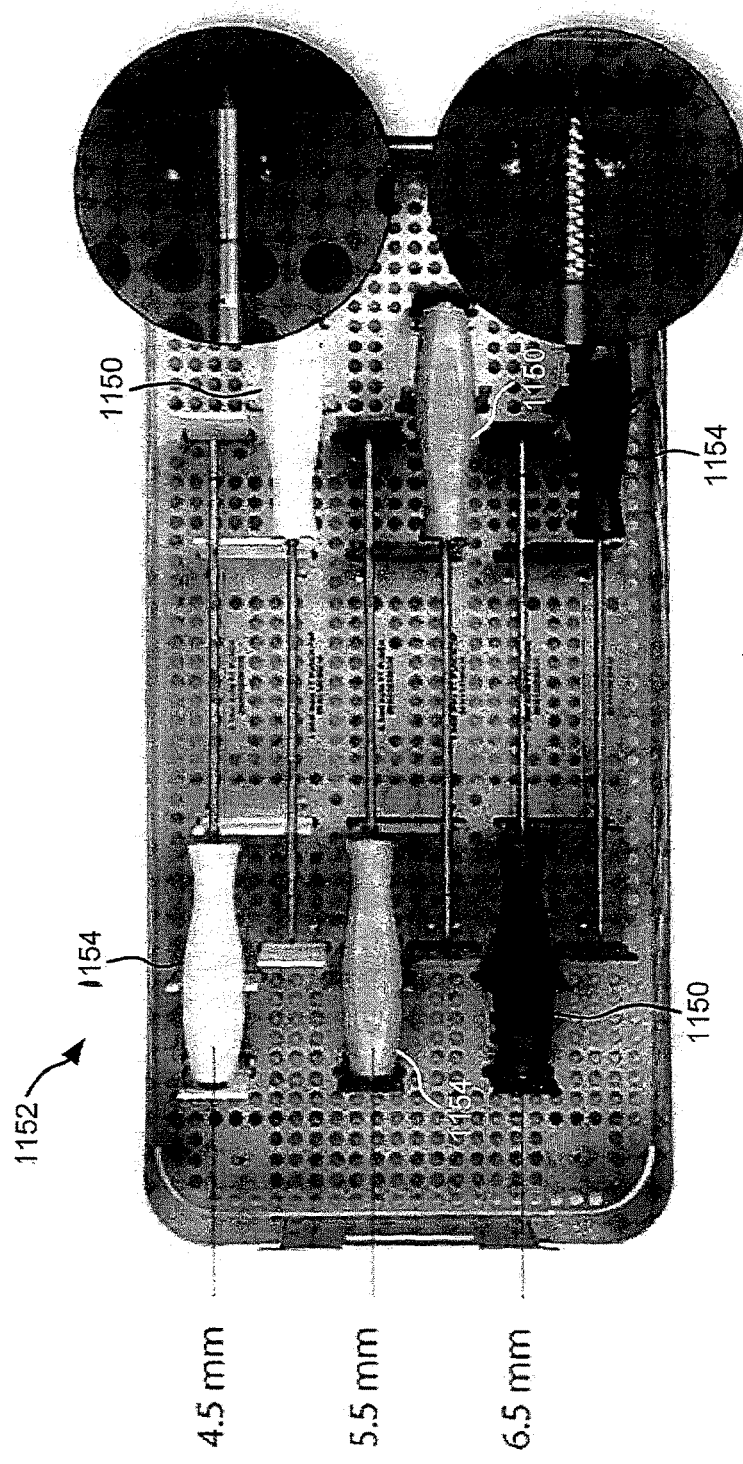
FIG. 16 illustrates a top view of a kit including the suture/anchor apparatus insertion tool of FIG. 15; and, FIG. 17 illustrates a flowchart of an exemplary method of manufacturing a suture according to an embodiment of the present invention.

FIG. 16 illustrates a kit 1152 that includes various tools for implanting a suture/anchor apparatus into a subject. The kit 1152 may include, for example, one or more punches 1154 for forming a hole in bone of a subject. The punches 1154 may each have different diameters (for example, 4.5 mm, 5.5 mm, and 6.5 mm) for forming holes of different sizes. The kit 1152 may also include, for example, one or more suture/anchor apparatus insertion tools 1150, such as the insertion tool 1050 described above. The insertion tools 1150 may each detachably carry anchors of different types and/or different sizes.

Figure 17:
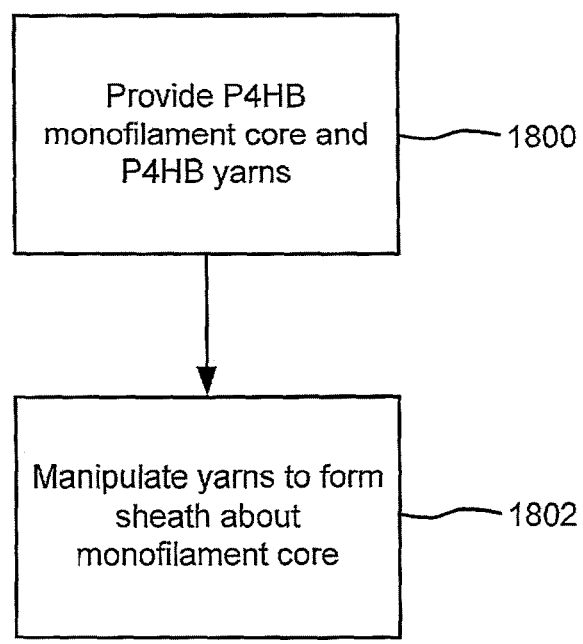

FIG. 17 illustrates a flowchart of an exemplary method of manufacturing a suture according to an embodiment of the present invention. The suture may be, for example, the suture 110 or any of the other exemplary sutures described herein. The method begins at block 1800 by providing a monofilament core that includes P4HB and a plurality of yarns that each include a plurality of threads, and the threads each include P4HB. At block 1802, the yarns are manipulated to form a sheath about the monofilament core. In some embodiments, the yarns are intertwined (for example, braided) about the monofilament core to form the sheath about the monofilament core.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

It should be noted that in the below examples, and as previously stated, the term "straight" testing as used herein means the sutures have been tested in an unknotted or straight configuration. The term "knot" or "knotted" testing as used herein means that the sutures have been tested with the suture having knots tied therein.

Example 1

In one exemplary embodiment of the present invention, a suture included a size 0 P4HB monofilament core. The core was surrounded by a braided multifilament sheath that includes twelve multifilament yarns. The yarns each included threads, and each thread included P4HB. Each yarn was 120 denier and included 60 threads. The braided multifilament sheath had 69.7 picks per inch. Overall, the suture was a size 2 suture and had a diameter of about 0.68 mm.

Test data indicated that such a suture had an ultimate tensile strength (straight pull) of about 211.8 Newtons and an elongation to break (straight pull) of about 48.1 percent.

Additional test data, based on testing nine lots of such sutures (each lot including either 10 or 29 sutures for a total of 147 data points), indicated that such a suture had an ultimate tensile strength (straight pull) of 181.0±9.1 Newtons (individual data points ranged from 195.7 to 139.9 Newtons) and an elongation to break (straight pull) of 45.3±2.7 percent (individual data points ranged from 50.9 to 34.8 percent) and, in a knotted configuration (e.g., the suture is tied with knots), an ultimate tensile strength of 99.1±6.8 Newtons (individual data points ranged from 113.8 to 79.0 Newtons) and an elongation to break of 32.0±1.5 percent (individual data points ranged from 35.8 to 27.2 percent). See Tables 1 and 2 below.

TABLE 1

Test data for nine lots of "Example 1" sutures.

| Lot | Suture | Straight Ultimate Tensile Strength (N) | Straight Elongation (%) | Knot Tensile Strength (N) | Knot Elongation (%) | USP Diameter (mm) (Avg of 6) | Notes |
|---|---|---|---|---|---|---|---|
| 1 | 1 | 170.5 | 42.15 | 110.13 | 34.46 | 0.674 | |
|  | 2 | 178.04 | 45.22 | 110.25 | 33.21 | 0.69 | |
|  | 3 | 175.22 | 44.68 | 103.53 | 32.67 | 0.687 | |
|  | 4 | 173.64 | 44.1 | 105.87 | 32.5 | 0.696 | |
|  | 5 | 180.44 | 46.19 | 104.19 | 32.83 | 0.674 | |
|  | 6 | 172.73 | 44.13 | 103.73 | 32.91 | 0.693 | |
|  | 7 | 177.56 | 46.17 | 106.73 | 33.46 | 0.684 | |
|  | 8 | 175.24 | 45.49 | 107.73 | 33.12 | 0.683 | |
|  | 9 | 176.63 | 44.87 | 106.33 | 33.03 | 0.672 | |
|  | 10 | 171.88 | 43.18 | 106.84 | 33.54 | 0.673 | |
|  | 11 | 178.21 | 47.44 | 109.42 | 32.94 | 0.672 | |
|  | 12 | 185 | 50.03 | 103.73 | 33.38 | 0.692 | |
|  | 13 | 174.38 | 44.54 | 113.84 | 33.84 | 0.682 | |
|  | 14 | 178.24 | 45.76 | 107.6 | 33.53 | 0.679 | |
|  | 15 | 176.47 | 44.53 | 105.48 | 33.36 | 0.675 | |
|  | 16 | 174.52 | 44.43 | 107.54 | 33.38 | 0.682 | |
|  | 17 | 165.75 | 40.65 | 107.76 | 33.47 | 0.679 | |
|  | 18 | 156.34 | 38.18 | 102.78 | 31.74 | 0.681 | |
|  | 19 | 179.67 | 46.26 | 108.28 | 32.99 | 0.673 | |
|  | 20 | 181.96 | 47.01 | 104.59 | 33.39 | 0.679 | |
|  | 21 | 181.45 | 45.43 | 107.52 | 32.27 | 0.675 | |
|  | 22 | 177.65 | 44.7 | 104.63 | 33.01 | 0.676 | |
|  | 23 | 177.9 | 45.56 | 103.68 | 32.65 | 0.679 | |
|  | 24 | 179.43 | 47.17 | 109.55 | 33.67 | 0.686 | Broken Filament |
|  | 25 | 177.9 | 44.79 | 101.93 | 31.7 | 0.682 | Broken Filament |
|  | 26 | 179.75 | 46.21 | 110.67 | 33.24 | 0.679 | Broken Filament |
|  | 27 | 173.32 | 43.52 | 102.9 | 32.88 | 0.673 | Broken Filament |
|  | 28 | 176.29 | 44.89 | 104.85 | 32.89 | 0.678 | Broken Filament |
|  | 29 | 173.75 | 43.26 | 104.53 | 32.88 | 0.676 | Broken Filament |
| 2 | 1 | 180.27 | 45.26 | 87.35 | 30.46 | 0.68 | |
|  | 2 | 176.53 | 44.57 | 110.63 | 33.93 | 0.682 | |
|  | 3 | 181.97 | 46.44 | 109.39 | 33.19 | 0.68 | |
|  | 4 | 179.06 | 45.76 | 105.93 | 33.38 | 0.677 | |
|  | 5 | 182.08 | 45.86 | 102.25 | 32.3 | 0.676 | |
|  | 6 | 180.34 | 46.74 | 99.47 | 31.06 | 0.679 | |
|  | 7 | 177.96 | 45.09 | 106.31 | 33.22 | 0.686 | |
|  | 8 | 179.64 | 45.94 | 102.21 | 32.72 | 0.68 | |
|  | 9 | 179.71 | 45.08 | 104.88 | 32.22 | 0.677 | |
|  | 10 | 182.49 | 46.73 | 100.53 | 32.38 | 0.669 | Broken Filament |
| 3 | 1 | 180.43 | 45.99 | 105.25 | 32.11 | 0.685 | |
|  | 2 | 175.07 | 44.06 | 106.68 | 33.16 | 0.675 | |

TABLE 1-continued

Test data for nine lots of "Example 1" sutures.

| Lot | Suture | Straight Ultimate Tensile Strength (N) | Straight Elongation (%) | Knot Tensile Strength (N) | Knot Elongation (%) | USP Diameter (mm) (Avg of 6) | Notes |
|---|---|---|---|---|---|---|---|
| | 3 | 177.97 | 45.11 | 103.93 | 35.25 | 0.68 | |
| | 4 | 181.04 | 45.29 | 107.38 | 33.05 | 0.683 | |
| | 5 | 181.33 | 46.32 | 110.58 | 34.38 | 0.686 | |
| | 6 | 178.37 | 44.78 | 104.92 | 33.62 | 0.681 | |
| | 7 | 179.72 | 44.45 | 102.1 | 33.17 | 0.683 | |
| | 8 | 174.48 | 43.3 | 103.53 | 31.99 | 0.679 | |
| | 9 | 179.02 | 45.68 | 104.29 | 32.64 | 0.674 | Broken Filament |
| | 10 | 175.95 | 44.35 | 110.65 | 33.49 | 0.68 | Broken Filament |
| 4 | 1 | 181.98 | 47.48 | 88.8 | 31.02 | 0.674 | |
| | 2 | 182.98 | 47.38 | 96.44 | 31.87 | 0.683 | |
| | 3 | 183.8 | 50.35 | 97.66 | 33.62 | 0.676 | |
| | 4 | 187.49 | 48.7 | 89.17 | 31.39 | 0.679 | |
| | 5 | 195.67 | 50 | 99.09 | 33.1 | 0.681 | |
| | 6 | 139.92 | 35.98 | 95.18 | 32.62 | 0.673 | |
| | 7 | 192.22 | 50.6 | 96.85 | 33.45 | 0.682 | |
| | 8 | 186.33 | 48.44 | 97.69 | 33.62 | 0.681 | |
| | 9 | 191.03 | 49.65 | 104.09 | 34.68 | 0.683 | |
| | 10 | 188.76 | 48.51 | 99.53 | 33.04 | 0.669 | |
| | 11 | 190.04 | 49.35 | 95.53 | 30.69 | 0.682 | |
| | 12 | 193.88 | 49.42 | 100.28 | 33.2 | 0.683 | |
| | 13 | 189.33 | 49.02 | 98.67 | 33.01 | 0.686 | |
| | 14 | 186.37 | 47.82 | 100.03 | 32.73 | 0.678 | |
| | 15 | 181.87 | 47.05 | 97.37 | 32.9 | 0.68 | |
| | 16 | 145.01 | 38.28 | 92.18 | 32.56 | 0.685 | |
| | 17 | 185.65 | 48.16 | 95.71 | 32.43 | 0.67 | |
| | 18 | 181.89 | 47.94 | 92.63 | 31.36 | 0.683 | |
| | 19 | 178.26 | 44.52 | 95.33 | 32.44 | 0.674 | Broken Filament |
| | 20 | 160.06 | 42.82 | 95.77 | 35.01 | 0.664 | Broken Filament |
| | 21 | 189.26 | 48.57 | 94.79 | 32.65 | 0.673 | Broken Filament |
| | 22 | 191.64 | 50.9 | 96.23 | 33.07 | 0.683 | Broken Filament |
| | 23 | 188.5 | 48.94 | 91.9 | 33.64 | 0.68 | Broken Filament |
| | 24 | 191.89 | 49.7 | 98.54 | 34.12 | 0.677 | Broken Filament |
| | 25 | 187.98 | 48.68 | 106.23 | 35.82 | 0.684 | Broken Filament |
| | 26 | 182.76 | 47.7 | 96.57 | 33.9 | 0.672 | Broken Filament |
| | 27 | 187.35 | 46.97 | 94.03 | 33.01 | 0.673 | Broken Filament |
| | 28 | 190.16 | 40.2 | 90.54 | 32.15 | 0.681 | Core pop |
| | 29 | 183.3 | 48.79 | 94.42 | 32.23 | 0.678 | Core pop |
| 5 | 1 | 187.85 | 46.76 | 99.84 | 33.08 | 0.674 | |
| | 2 | 158.61 | 39.55 | 90.26 | 30.64 | 0.67 | |
| | 3 | 181.44 | 46.48 | 88.92 | 30.18 | 0.672 | |
| | 4 | 191.92 | 49.16 | 92.19 | 30.36 | 0.675 | |
| | 5 | 195.16 | 49.88 | 98.62 | 31.22 | 0.67 | |
| | 6 | 189.14 | 46.9 | 93.22 | 30.95 | 0.66 | Broken Filament |
| | 7 | 193.52 | 48.42 | 96.67 | 31.37 | 0.654 | Broken Filament |
| | 8 | 190.62 | 46.95 | 97.08 | 30.98 | 0.654 | Broken Filament |
| | 9 | 191.12 | 48.64 | 92.9 | 30.49 | 0.65 | Broken Filament |
| | 10 | 187.68 | 46.27 | 94.79 | 30.09 | 0.652 | Broken Filament |
| 6 | 1 | 194.42 | 46.98 | 98.73 | 32.18 | 0.651 | |
| | 2 | 189.06 | 45.42 | 87.03 | 29.98 | 0.657 | |
| | 3 | 191.04 | 44.84 | 80.21 | 27.19 | 0.653 | |
| | 4 | 179.99 | 42.52 | 92.91 | 30.57 | 0.657 | |
| | 5 | 179.32 | 42.97 | 99.16 | 31.24 | 0.659 | |
| | 6 | 143.32 | 37.26 | 93.35 | 31.1 | 0.657 | |
| | 7 | 190.45 | 46.85 | 95.41 | 31.81 | 0.649 | |
| | 8 | 190.04 | 44.85 | 96.12 | 31.72 | 0.665 | Broken Filament |
| | 9 | 182.64 | 45.6 | 99.65 | 33.05 | 0.654 | Broken Filament |

TABLE 1-continued

Test data for nine lots of "Example 1" sutures.

| Lot | Suture | Straight Ultimate Tensile Strength (N) | Straight Elongation (%) | Knot Tensile Strength (N) | Knot Elongation (%) | USP Diameter (mm) (Avg of 6) | Notes |
|---|---|---|---|---|---|---|---|
| | 10 | 187.85 | 46.89 | 101.83 | 31.52 | 0.65 | Broken Filament |
| 7 | 1 | 185.87 | 47.11 | 93.27 | 30.4 | 0.654 | |
| | 2 | 182.98 | 44.35 | 95.01 | 31.02 | 0.653 | |
| | 3 | 183.32 | 44.1 | 101.62 | 31.39 | 0.65 | |
| | 4 | 142.23 | 34.82 | 97.96 | 30.67 | 0.665 | |
| | 5 | 179.15 | 42.46 | 111.03 | 33.36 | 0.65 | |
| | 6 | 188.83 | 46.48 | 90.43 | 29.96 | 0.647 | |
| | 7 | 176.26 | 44.35 | 88.35 | 30.27 | 0.652 | |
| | 8 | 184.92 | 44.25 | 94.37 | 32.48 | 0.651 | |
| | 9 | 185.33 | 45.15 | 104 | 32.31 | 0.651 | |
| | 10 | 180.44 | 44.65 | 106.11 | 32.9 | 0.648 | |
| | 11 | 177.85 | 43.18 | 97.52 | 31.87 | 0.644 | |
| | 12 | 182.67 | 43.73 | 98.89 | 31.8 | 0.65 | |
| | 13 | 182.27 | 43 | 95.21 | 30.47 | 0.65 | |
| | 14 | 188.12 | 46.66 | 95.61 | 30.24 | 0.642 | |
| | 15 | 183.77 | 45.17 | 102.84 | 32.75 | 0.645 | |
| | 16 | 181.84 | 42.71 | 97.08 | 32.05 | 0.642 | |
| | 17 | 178.44 | 41.68 | 97.15 | 31.33 | 0.655 | |
| | 18 | 188.53 | 44.25 | 96.23 | 30.55 | 0.645 | |
| | 19 | 187.1 | 47.22 | 94.76 | 31.14 | 0.648 | |
| | 20 | 182.7 | 45.38 | 96.74 | 31.49 | 0.651 | |
| | 21 | 182.12 | 42.4 | 86.37 | 28.87 | 0.658 | |
| | 22 | 181.43 | 42.8 | 98.38 | 31.42 | 0.658 | |
| | 23 | 181.73 | 43.6 | 98.36 | 31.7 | 0.644 | |
| | 24 | 183.28 | 44.04 | 104.13 | 31.98 | 0.651 | |
| | 25 | 179.23 | 45.43 | 102.95 | 32.45 | 0.659 | |
| | 26 | 181.01 | 43.06 | 100.76 | 32.36 | 0.655 | |
| | 27 | 180.21 | 44.19 | 93.92 | 31.24 | 0.668 | Broken Filament |
| | 28 | 179.85 | 43.51 | 100.98 | 31.89 | 0.661 | Broken Filament |
| | 29 | 184.67 | 47 | 90.89 | 30.48 | 0.651 | Broken Filament |
| 8 | 1 | 184.76 | 43.93 | 93.76 | 31.26 | 0.644 | |
| | 2 | 184.61 | 45.05 | 99.49 | 30.67 | 0.658 | |
| | 3 | 183.06 | 46.11 | 88.13 | 29.05 | 0.65 | |
| | 4 | 182.57 | 45.16 | 90.65 | 29.55 | 0.641 | |
| | 5 | 183.22 | 45.43 | 99.1 | 30.83 | 0.642 | |
| | 6 | 184.25 | 45.2 | 87.58 | 28.28 | 0.643 | |
| | 7 | 185.75 | 46.22 | 78.99 | 27.44 | 0.647 | |
| | 8 | 180.58 | 43.72 | 82.54 | 28.33 | 0.646 | Broken Filament |
| | 9 | 181.89 | 44.23 | 91.62 | 30.15 | 0.648 | Broken Filament |
| | 10 | 184.56 | 45.82 | 100.91 | 31.41 | 0.643 | Broken Filament |
| 9 | 1 | 176.92 | 41.26 | 96.92 | 30.94 | 0.648 | |
| | 2 | 182.4 | 43.16 | 96.31 | 29.8 | 0.648 | |
| | 3 | 185.15 | 45.33 | 104.2 | 31.21 | 0.643 | |
| | 4 | 187.4 | 44.33 | 94.66 | 31.24 | 0.651 | |
| | 5 | 182.36 | 42.29 | 94.01 | 30.05 | 0.647 | |
| | 6 | 187 | 44.97 | 81.66 | 27.64 | 0.637 | |
| | 7 | 184.63 | 44.5 | 94.5 | 30.32 | 0.653 | |
| | 8 | 178.93 | 42.76 | 100.92 | 30.42 | 0.645 | |
| | 9 | 172.1 | 40.38 | 101.8 | 30.61 | 0.647 | Broken Filament |
| | 10 | 178.97 | 43.83 | 100.15 | 30.9 | 0.645 | Broken Filament |

TABLE 2

Test data statistics for nine lots of "Example 1" sutures.

| Lot | | Ultimate Straight Tensile Strength (N) | Straight Elongation (%) | Knot Tensile Strength (N) | Knot Elongation (%) |
|---|---|---|---|---|---|
| 1 | Average | 175.86 | 44.85 | 106.43 | 33.07 |
|   | Standard Deviation | 5.36 | 2.16 | 2.84 | 0.57 |
| 2 | Average | 180.01 | 45.75 | 102.90 | 32.49 |
|   | Standard Deviation | 1.99 | 0.74 | 6.55 | 1.07 |
| 3 | Average | 178.34 | 44.93 | 105.93 | 33.29 |
|   | Standard Deviation | 2.46 | 0.93 | 2.89 | 0.99 |
| 4 | Average | 183.29 | 47.31 | 96.25 | 32.94 |
|   | Standard Deviation | 13.05 | 3.62 | 3.91 | 1.14 |
| 5 | Average | 186.71 | 46.90 | 94.45 | 30.94 |
|   | Standard Deviation | 10.57 | 2.87 | 3.58 | 0.87 |
| 6 | Average | 182.81 | 44.42 | 94.44 | 31.04 |
|   | Standard Deviation | 14.75 | 2.95 | 6.56 | 1.59 |
| 7 | Average | 181.25 | 44.03 | 97.62 | 31.41 |
|   | Standard Deviation | 8.15 | 2.32 | 5.38 | 1.01 |
| 8 | Average | 183.53 | 45.09 | 91.28 | 29.70 |
|   | Standard Deviation | 1.56 | 0.88 | 7.30 | 1.38 |
| 9 | Average | 181.59 | 43.28 | 96.51 | 30.31 |
|   | Standard Deviation | 4.85 | 1.62 | 6.27 | 1.05 |
|   | Maximum | 195.7 | 50.9 | 113.8 | 35.8 |
|   | Maximum | 139.9 | 34.8 | 78.99 | 27.2 |
| Average of all data points | | 181.0 | 45.3 | 99.1 | 32.0 |
| Std. Dev. Of all data points | | 9.1 | 2.7 | 6.8 | 1.5 |

The above data were obtained using the following procedures. Diameter measurements were performed using a diameter fixture and a thickness gage. A 2.2 kg mass was used to tension each suture. Six measurements were taken on each suture, and the data in Table 1 for each suture is the average of the six measurements.

Tensile tests were performed using an ADMET Tester, a load cell, and grips. The gage length was set at 219 mm using a gap gage. The grips were displaced at a rate of 30 mm per minute to a load of 1.3345 Newtons (logging every 0.0033 minutes), then at a rate of 0.1 mm per minute for a duration of 0.1 minutes (logging every 0.0033 minutes), and then at a rate of 300 mm per minute to a load of 44482.2148 Newtons or until failure (recording every 0.0004 minutes). Failure was determined by a drop in the load to 50 percent of the peak load.

Additionally, sutures displayed reduced memory (compared to other sutures) when removed from packaging and improved handling and knot security (again, compared to other sutures).

Example 2

In another embodiment of the present invention, the suture included a size 5-0 P4HB monofilament core. The core is surrounded by a multifilament sheath that included eight multifilament yarns. Each yarn included P4HB threads. Each yarn is 120 denier and included 60 threads. Overall, the suture is a size 2-0 suture and had a diameter of about 0.423 mm.

Test data indicated that such a suture had an ultimate tensile strength (straight pull) of about 61.5 Newtons and an elongation to break (straight pull) of about 28.37 percent and, in a knotted configuration, had an ultimate tensile strength of about 44.0 Newtons and an elongation to break of about 71.5 percent.

Example 3

In an alternate embodiment of the present invention, a suture included a size 0 P4HB monofilament core. The core is surrounded by a braided multifilament sheath that included twelve multifilament yarns. The yarns each included threads, and each thread included P4HB. The multifilament sheath had 64.7 picks per inch. Overall, the suture was a size 2 suture and had a diameter of about 0.67 mm.

Test data indicated that such a suture had an ultimate tensile strength (straight pull) of about 207.4 Newtons and an elongation to break (straight pull) of about 46.6 percent.

Example 4

In another embodiment of the present invention, a suture included a size 0 monofilament core. The core included P4HB. The core is surrounded by a braided multifilament sheath that included twelve multifilament yarns. The yarns each included threads, and each thread included P4HB. The multifilament sheath had 56 picks per inch. Overall, the suture was a size 2 suture and had a diameter of about 0.67 mm.

Test data indicate that such a suture had an ultimate tensile strength (straight pull) of about 173.7 Newtons and an elongation to break (straight pull) of about 38.9 percent.

Example 5

In yet another embodiment of the present invention, a suture included a size 0 P4HB monofilament core. The core is surrounded by a braided multifilament sheath that included twelve multifilament yarns. The yarns each included threads, and each thread included P4HB. The multifilament sheath had 70.5 picks per inch. Overall, the suture was a size 2 suture and had a diameter of about 0.68 mm.

Test data indicate that such a suture had an ultimate tensile strength (straight pull) of about 210.0 Newtons and an elongation to break (straight pull) of about 49.0 percent.

Example 6

In another embodiment of the present invention, a suture included a size 1 P4HB monofilament core. The core is surrounded by a braided multifilament sheath that included eight multifilament yarns. The yarns each included threads, and each thread included P4HB. The multifilament sheath had 54.3 picks per inch. Overall, the suture was a size 2 suture and had a diameter of about 0.67 mm.

Test data indicated that such a suture had an ultimate tensile strength (straight pull) of about 254.0 Newtons and an elongation to break (straight pull) of about 33.7 percent.

Example 7

In an alternate embodiment of the present invention, a suture included a size 4-0 P4HB monofilament core. The core is surrounded by a braided multifilament sheath that included eight multifilament yarns. The yarns each included threads, and each thread included P4HB. The multifilament sheath had 64.5 picks per inch. Overall, the suture was a size 2-0 suture and had a diameter of about 0.46 mm.

Test data indicate that such a suture, in a straight configuration, had an ultimate tensile strength of about 71.4 Newtons and an elongation to break of about 44.0 percent.

Example 8

In another embodiment of the present invention, a suture included a size 0 P4HB monofilament core. The core is surrounded by a braided multifilament sheath that included sixteen multifilament yarns. The yarns each included threads, and each thread included P4HB. Overall, the suture is a size 3 suture and had a diameter of about 0.705 mm.

Test data indicated that such a suture in a straight configuration had an ultimate tensile strength of about 231.0 Newtons and an elongation to break of about 59.50 percent and, in a knotted configuration, had an ultimate tensile strength of about 91.1 Newtons and an elongation to break of about 39.4 percent.

Example 9

In another embodiment of the present invention, a suture included a size 0 P4HB monofilament core. The core is surrounded by a braided multifilament sheath that included twelve multifilament yarns. The yarns each included threads, and each thread included P4HB. Overall, the suture was a size 3-4 suture and had a diameter of about 0.815 mm.

Test data indicate that such a suture, in a straight configuration, had an ultimate tensile strength of about 259.7 Newtons and an elongation to break of about 58.38 percent and, in a knotted configuration, had an ultimate tensile strength of about 120.5 Newtons and an elongation to break of about 46.4 percent.

Example 10

In one exemplary embodiment of the present invention, a suture included a size 0 monofilament core. The core included P4HB. The core is surrounded by a braided multifilament sheath that included sixteen multifilament yarns. The yarns each included threads, and each thread included P4HB. Overall, the suture was a size 2 suture and had a diameter of about 0.68 mm.

Test data indicate that such a suture, in a knotted configuration, had an ultimate tensile strength of about 87.8 Newtons.

For comparison, other sutures were also tested to determine their ultimate tensile strength, elongation to break, knot ultimate tensile strength, knot elongation to break, and diameter. These sutures include FiberWire® available from Arthrex Inc. of Naples, Fla., USA, Orthocord® available from DePuy Mitek, Inc. of Raynham, Mass., USA, and Ethibond Excel™ available from Ethicon, Inc. of Somerville, N.J., USA. All of the sutures were size 2 sutures, and all of the sutures were tested using the same procedure described above in Example 1 (except for the lot sizes used; see Table 3 below).

The test data indicate that Arthrex FiberWire® sutures have an ultimate tensile strength (straight pull) of about 279 Newtons (an average of 278.85 Newtons with a standard deviation of 15.81 Newtons), an elongation to break (straight pull) of about 10 percent (an average of 9.64 percent with a standard deviation of 0.85 percent), a knot ultimate tensile strength of about 133 Newtons (an average of 133.21 Newtons with a standard deviation of 7.08 Newtons), and a knot elongation to break of about 6 percent (an average of 5.84 percent with a standard deviation of 0.67 percent).

The test data indicate that the Depuy Mitek Orthocord® have an ultimate tensile strength (straight pull) of about 219 Newtons (an average of 218.74 Newtons with a standard deviation of 21.56 Newtons), an elongation to break (straight pull) of about 15 percent (an average of 15.06 percent with a standard deviation of 0.85 percent), a knot ultimate tensile strength of about 147 Newtons (an average of 146.82 Newtons with a standard deviation of 8.13 Newtons), and a knot elongation to break of about 14 percent (an average of 14.07 percent with a standard deviation of 1.76 percent).

The test data indicate that Ethicon Ethibond Excel™ sutures have an ultimate tensile strength (straight pull) of about 141 Newtons (an average of 141.45 Newtons with a standard deviation of 3.67 Newtons), an elongation to break (straight pull) of about 20 percent (an average of 20.19 percent with a standard deviation of 0.80 percent), a knot ultimate tensile strength of about 68 Newtons (an average of 67.98 Newtons with a standard deviation of 2.36 Newtons), and a knot elongation to break of about 14 percent (an average of 13.82 percent with a standard deviation of 0.38 percent).

TABLE 3

Test data for other sutures.

| Suture | | USP Diameter (mm) (Avg of 6) | Straight Ultimate Tensile Strength (N) | Straight Elongation (%) | Knot Tensile Strength (N) | Knot Elongation (%) |
|---|---|---|---|---|---|---|
| Arthex FiberWire® | 1 | 0.603 | 208.39* | 5.49* | 120.15 | 6.49 |
| | 2 | 0.556 | 287.76 | 9.43 | 130.69 | 7.09 |
| | 3 | 0.537 | 222.50* | 5.73* | 128.91 | 5.74 |
| | 4 | 0.536 | 257.11 | 9.22 | 133.31 | 5.49 |
| | 5 | 0.553 | 273.39 | 10.87 | 134.51 | 4.77 |
| | 6 | 0.541 | 257.64 | 8 | 150.57 | 5.19 |
| | 7 | | 294.61 | 11.06 | 133.62 | 5.85 |
| | 8 | | 294.74 | 9.62 | 135.27 | 6.1 |
| | 9 | | 299.85 | 10.23 | 130.82 | 4.82 |
| | 10 | | 283.04 | 9.34 | 125.71 | 5.8 |
| | 11 | | 256.80 | 9.14 | 138.21 | 6.58 |
| | 12 | | 283.57 | 9.44 | 136.69 | 6.11 |
| | Avg. | 0.554 | 278.85 | 9.64 | 133.21 | 5.84 |
| | Std. Dev. | 0.023 | 15.81 | 0.85 | 7.08 | 0.67 |
| DePuy Orthocord® | 1 | 0.552 | 219.52 | 14.5 | 142.79 | 14.82 |
| | 2 | 0.56 | 217.47 | 14.99 | 136.78 | 14.41 |
| | 3 | 0.572 | 238.60 | 15.49 | 144.70 | 15.65 |
| | 4 | 0.571 | 214.58 | 14.15 | 145.68 | 15.22 |
| | 5 | 0.563 | 243.23 | 14.94 | 147.06 | 16.95 |
| | 6 | 0.564 | 224.06 | 14.44 | 141.81 | 16.29 |
| | 7 | | 251.99 | 16 | 145.59 | 12.95 |
| | 8 | | 208.22 | 16.54 | 153.29 | 12.71 |
| | 9 | | 161.69 | 13.46 | 168.01 | 14.25 |
| | 10 | | 216.72 | 16.18 | 154.71 | 12.96 |
| | 11 | | 210.80 | 14.76 | 143.50 | 11.15 |
| | 12 | | 217.96 | 15.22 | 137.94 | 11.51 |
| | Avg. | 0.564 | 218.74 | 15.06 | 146.82 | 14.07 |
| | Std. Dev. | 0.007 | 21.56 | 0.85 | 8.13 | 1.76 |
| Ethicon Ethibond Excel ™ | 1 | 0.551 | 140.30 | 19.51 | 66.06 | 13.54 |
| | 2 | 0.54 | 142.97 | 20.51 | 70.59 | 14.35 |
| | 3 | 0.549 | 145.55 | 21.07 | 70.59 | 14.1 |
| | 4 | 0.535 | 144.79 | 20.76 | 66.37 | 13.73 |
| | 5 | 0.544 | 135.45 | 19 | 68.06 | 13.89 |
| | 6 | 0.537 | 143.77 | 20.88 | 70.46 | 13.95 |
| | 7 | | 137.09 | 19.21 | 67.21 | 13.62 |
| | 8 | | 140.21 | 19.92 | 68.41 | 14.08 |
| | 9 | | 134.83 | 18.91 | 71.39 | 14.29 |
| | 10 | | 145.46 | 20.92 | 66.95 | 13.73 |
| | 11 | | 143.86 | 21.11 | 62.90 | 12.87 |
| | 12 | | 143.14 | 20.47 | 66.81 | 13.71 |
| | Avg. | 0.543 | 141.45 | 20.19 | 67.98 | 13.82 |
| | Std. Dev. | 0.006 | 3.67 | 0.80 | 2.36 | 0.38 |

The two denoted sutures (*) did not completely break when failure was detected. Beginning with FiberWire® suture 4, the break detection parameter was modified from a drop in load to 50 percent of the peak load to a drop in load to 25 percent of the peak load, which permitted the suture to break before a failure is detected. This parameter remained for FiberWire® samples 4 through 12, as FiberWire® was the last product tested. The results from these sutures were not included in the average or standard deviation calculations.

What is claimed is:

1. A suture, comprising:
   a multifilament sheath including a plurality of yarns, the plurality of yarns comprising poly-4-hydroxybutyrate; and
   a monofilament core comprising poly-4-hydroxybutyrate, wherein the multifilament sheath is disposed thereabout the monofilament core, wherein the multifilament sheath and the monofilament core comprise the same polymeric material,
   wherein the suture has an ultimate tensile strength of from about 140 Newtons to about 190 Newtons, wherein the monofilament core is about a size 0, wherein the multifilament sheath comprises twelve yarns.

2. The suture of claim 1, wherein the plurality of yarns includes a plurality of threads, and each of the threads comprise poly-4-hydroxybutyrate.

3. The suture of claim 1, wherein each of the twelve yarns is about 120 denier and includes about 60 threads.

4. The suture of claim 1, wherein the suture has an ultimate tensile strength of about 160 Newtons.

5. The suture of claim 1, wherein the suture has an elongation to break of about 30 percent to about 50 percent.

6. The suture of claim 5, wherein the suture has an elongation to break of at least about 34 percent.

7. The suture of claim 1, wherein the suture is about a size 2.

8. The suture of claim 1, further comprising a needle disposed on at least one end thereof.

9. The suture of claim 1, wherein the suture includes an enlarged portion disposed between a first end and a second end of the suture.

10. The suture of claim 9, wherein the enlarged portion includes poly-4-hydroxybutyrate filaments disposed interior to the multifilament sheath.

11. The suture of claim 1, wherein the multifilament sheath has from about 54 to about 71 picks per inch.

12. The suture of claim 1, wherein two of the yarns have violet colored threads and ten of the yarns have natural colored threads.

13. The suture of claim 1, wherein the suture comprises a diameter within the range of 0.637 to 0.696 mm.

14. The suture of claim 1, wherein the multifilament sheath is configured to maintain a cylindrical configuration when the monofilament core is removed.

15. A suture, comprising:
    a bioabsorbable monofilament core;
    a bioabsorbable multifilament sheath disposed thereabout the bioabsorbable monofilament core; and
    wherein the suture consists essentially of poly-4-hydroxybutyrate, wherein the bioabsorbable monofilament core and the bioabsorbable multifilament sheath comprise the same material,
    wherein the suture has an ultimate tensile strength of from about 140 Newtons to about 190 Newtons, wherein the bioabsorbable monofilament core is about a size 0, wherein the bioabsorbable multifilament sheath comprises twelve yarns.

16. The suture of claim 15, wherein the suture has an elongation to break of at least about 34 percent.

17. A method of manufacturing a suture, comprising:
    forming a multifilament sheath about a monofilament core, the monofilament core comprising poly-4-hydroxybutyrate, and the multifilament sheath including a plurality of yarns each comprising poly-4-hydroxybutyrate, wherein the multifilament sheath and the monofilament core comprise the same polymeric material, wherein the suture has an ultimate tensile strength of from about 140 Newtons to about 190 Newtons, wherein the monofilament core is about a size 0, wherein the multifilament sheath comprises twelve yarns.

18. The method of claim 17, wherein each of the twelve yarns is about 120 denier and includes about 60 threads.

19. The method of claim 17, wherein forming the multifilament sheath about the monofilament core includes intertwining a plurality of yarns about the monofilament core, the plurality of yarns including a plurality of threads.

20. The method of claim 17, wherein the multifilament sheath maintains a cylindrical configuration when the monofilament core is removed.

* * * * *

UNITED STATES PATENT AND TRADEMARK OFFICE
CERTIFICATE OF CORRECTION

| | | |
|---|---|---|
| PATENT NO. | : 10,485,535 B2 | |
| APPLICATION NO. | : 15/039167 | |
| DATED | : November 26, 2019 | |
| INVENTOR(S) | : Corey R. Wilson-Wirth et al. | |

It is certified that error appears in the above-identified patent and that said Letters Patent is hereby corrected as shown below:

In the Specification

In Column 1, Line 18 (Approx.), delete "HELD" and insert --FIELD--.

In Column 3, Line 36 (Approx.), delete "D" and insert --$D_1$--.

In Column 4, Line 33, delete "(beta.-IFN," and insert --(.beta.-IFN,--.

In Column 5, Lines 5-6, delete "propanolol," and insert --propranolol,--.

In Column 5, Lines 9-10, delete "serpentine," and insert --serpentina,--.

In Column 5, Line 30, delete "propanolol," and insert --propranolol,--.

In Column 5, Line 33, delete "benzodiazapines" and insert --benzodiazepines--.

In Column 5, Line 59, delete "phenyloin, phenyloin" and insert --phenytoin, phenytoin--.

In Column 5, Line 60, delete "phenobarbitol," and insert --phenobarbital,--.

In Column 5, Line 61, delete "mephenyloin," and insert --mephenytoin,--.

In Column 5, Lines 64-65, delete "antihistaminesiantipruritics," and insert --antihistamines/antipruritics,--.

In Column 6, Line 33, delete "(e.g.," and insert --e.g.,--.

In Column 6, Lines 36-37, delete "bitolterolmesylate," and insert --bitolterol mesylate,--.

In Column 6, Line 47, delete "nedocrormil," and insert --nedocromil,--.

Signed and Sealed this
Twenty-first Day of April, 2020

Andrei Iancu
*Director of the United States Patent and Trademark Office*

CERTIFICATE OF CORRECTION (continued)
U.S. Pat. No. 10,485,535 B2

In Column 6, Line 48, delete "proprionate;" and insert --propionate;--.

In Column 6, Line 51, delete "enathate," and insert --enanthate,--.

In Column 7, Line 3, delete "pravastitin," and insert --pravastatin,--.

In Column 7, Line 6, delete "adds" and insert --acids--.

In Column 7, Line 18, delete "mefformin," and insert --metformin,--.

In Column 7, Line 19, delete "lorazepan," and insert --lorazepam,--.

In Column 7, Line 25, delete "flecainid," and insert --flecainide,--.

In Column 7, Line 28, delete "monteleukast," and insert --montelukast,--.

In Column 7, Line 39, delete "after" and insert --alter--.

In Column 7, Line 53, delete "Pharmacopia)" and insert --Pharmacopeia)--.

In Column 8, Line 4, delete "10" and insert --to--.